United States Patent
Hidaka et al.

(10) Patent No.: US 10,631,924 B2
(45) Date of Patent: Apr. 28, 2020

(54) HIGH-FREQUENCY TREATMENT TOOL

(71) Applicant: OLYMPUS CORPORATION, Tokyo (JP)

(72) Inventors: Yuya Hidaka, Tokyo (JP); Haruki Okamoto, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 250 days.

(21) Appl. No.: 15/840,343

(22) Filed: Dec. 13, 2017

(65) Prior Publication Data

US 2018/0110559 A1  Apr. 26, 2018

Related U.S. Application Data

(63) Continuation of application No. PCT/JP2016/066463, filed on Jun. 2, 2016.

(30) Foreign Application Priority Data

Jun. 18, 2015 (JP) .................................. 2015-122945

(51) Int. Cl.
*A61B 18/14* (2006.01)
*A61B 1/00* (2006.01)
(Continued)

(52) U.S. Cl.
CPC ........ *A61B 18/148* (2013.01); *A61B 1/00087* (2013.01); *A61B 18/1492* (2013.01);
(Continued)

(58) Field of Classification Search
CPC .............. A61B 18/148; A61B 18/1492; A61B 2018/00029; A61B 2018/0016;
(Continued)

(56) References Cited

U.S. PATENT DOCUMENTS 8,016,825 B2 *  9/2011  Okada ................ A61B 18/1402
                                                 606/45
9,387,034 B2 *  7/2016  Okada .................... A61B 18/14
(Continued)

FOREIGN PATENT DOCUMENTS

EP    1726266 A1    11/2006
EP    1752108 A1    2/2007
(Continued)

OTHER PUBLICATIONS

International Search Report dated Aug. 9, 2016 issued in PCT/JP2016/066463.
(Continued)

*Primary Examiner* — Michael F Peffley
(74) *Attorney, Agent, or Firm* — Scully, Scott, Murphy & Presser, P.C.

(57) ABSTRACT

Provided is a high-frequency treatment tool including: a sheath; an electrode member being advancable and retractable in the sheath; a distal end member disposed at a distal end of the sheath, wherein the electrode member includes a columnar portion; an electrode distal end portion provided at a distal end of the columnar portion and radially extending in an outward direction; and a stopper portion disposed at a proximal end side of the columnar portion, the stopper portion having the shape of a solid of revolution about a center axis of the electrode member, the distal end member has a tapered inner surface narrowing toward the distal end, a recessed portion is formed in a portion of the stopper portion, the electrode distal end portion has a small-diameter portion recessed in a radial direction, and the channel and the small-diameter portion are located at the same position in the circumferential direction.

9 Claims, 7 Drawing Sheets

(51) Int. Cl.
    *A61B 18/00* (2006.01)
    *A61B 17/00* (2006.01)
(52) U.S. Cl.
    CPC ............ *A61B 2017/00269* (2013.01); *A61B 2018/0016* (2013.01); *A61B 2018/00029* (2013.01); *A61B 2018/00982* (2013.01); *A61B 2018/1475* (2013.01); *A61B 2218/002* (2013.01)
(58) Field of Classification Search
    CPC .. A61B 2018/00982; A61B 2018/1475; A61B 1/00087; A61B 2017/00269; A61B 2218/002
    See application file for complete search history.

(56) References Cited

U.S. PATENT DOCUMENTS

| | | | |
|---|---|---|---|
| 9,526,562 B2* | 12/2016 | Yamamoto | A61B 18/12 |
| 2004/0167514 A1 | 8/2004 | Okada | |
| 2004/0172018 A1 | 9/2004 | Okada | |
| 2004/0210284 A1 | 10/2004 | Okada | |
| 2006/0270969 A1 | 11/2006 | Toyonaga et al. | |
| 2007/0038213 A1* | 2/2007 | Machiya | A61B 18/1492 606/45 |
| 2009/0105739 A1* | 4/2009 | Toyonaga | A61B 18/1492 606/169 |
| 2012/0203214 A1 | 8/2012 | Okada | |
| 2014/0207134 A1 | 7/2014 | Wake | |
| 2014/0288554 A1 | 9/2014 | Okada | |
| 2016/0008063 A1 | 1/2016 | Wake et al. | |
| 2017/0245842 A1 | 8/2017 | Ito et al. | |
| 2018/0110559 A1* | 4/2018 | Hidaka | A61B 1/00087 |

FOREIGN PATENT DOCUMENTS

| | | |
|---|---|---|
| EP | 1985252 A1 | 10/2008 |
| EP | 1987795 A1 | 11/2008 |
| EP | 2 050 409 A1 | 4/2009 |
| EP | 2896379 A1 | 7/2015 |
| EP | 2 910 212 A1 | 8/2015 |
| EP | 3 056 158 A1 | 8/2016 |
| EP | 3 222 241 A1 | 9/2017 |
| JP | 2004248911 A | 9/2004 |
| JP | 2004261372 A | 9/2004 |
| JP | 2007044393 A | 2/2007 |
| JP | 2009-112788 A | 5/2009 |
| JP | 2009-112794 A | 5/2009 |
| JP | 4315725 B2 | 8/2009 |
| JP | 4836492 B2 | 12/2011 |
| JP | 2012070793 A | 4/2012 |
| JP | 2012075657 A | 4/2012 |
| JP | 2013111308 A | 6/2013 |
| JP | 5646788 B2 | 12/2014 |
| WO | 2012/042956 A1 | 4/2012 |
| WO | 2012/042984 A1 | 4/2012 |
| WO | 2015/053365 A1 | 4/2015 |

OTHER PUBLICATIONS

Extended Supplementary European Search Report dated Mar. 7, 2019 in European Patent Application No. 16 81 1453.6.

* cited by examiner

HIGH-FREQUENCY TREATMENT TOOL

CROSS-REFERENCE TO RELATED APPLICATIONS

This is a continuation of International Application PCT/JP2016/066463, with an international filing date of Jun. 2, 2016, which is hereby incorporated by reference herein in its entirety. This application claims the benefit of Japanese Patent Application No. 2015-122945, the content of which is incorporated herein by reference.

TECHNICAL FIELD

The present invention relates to a high-frequency treatment tool.

BACKGROUND ART

A high-frequency treatment tool that treats body tissue, such as mucosae, by applying high-frequency current to the body tissue is known (for example, refer to PTL 1).

This high-frequency treatment tool has a structure in which a bar electrode unit is inserted into a through hole of an electrically insulating cap member provided at a distal end of a sheath such that the bar electrode unit can be advanced or retracted in the axis direction and a liquid, which has been sent through the sheath, can be released forward through a liquid feed opening of the cap member.

A radially spreading distal end portion is provided at a distal end of the bar electrode unit. Thus, by forming at least part of the liquid feed opening to be exposed on the outer side of the distal end portion in a front view of the cap member, the liquid to be released from the liquid feed opening is prevented from becoming blocked by the back side of the distal end portion of the bar electrode unit. According to the high-frequency treatment tool described in PTL 1, the liquid feed opening has a non-circular structure constituted by a small-diameter portion that is adjacent to and supports the bar electrode unit and a large diameter portion exposed on the outer side of the distal end portion.

CITATION LIST

Patent Literature

{PTL 1} Japanese Unexamined Patent Application, Publication No. 2012-70793

SUMMARY OF INVENTION

An aspect of the present invention provides a high-frequency treatment tool that includes an elongated cylindrical sheath to be inserted into a body; a straight bar-shaped electrode member to which high-frequency current is to be supplied, the electrode member being disposed so as to be advancable and retractable in the sheath in a longitudinal axis direction; a distal end member that is disposed at a distal end side of the sheath and that has a through hole through which the electrode member is passed; and a liquid feeding unit that is connected to a proximal end of the sheath that is configured to release a liquid forward in the longitudinal axis direction of the sheath through a channel formed in the sheath and a gap between the electrode member and the through hole in communication with the channel. The electrode member includes a bar-shaped columnar portion; an electrode distal end portion being provided at a distal end of the columnar portion and radially extending in a radially outward direction; and a stopper portion disposed at a proximal end side of the columnar portion with respect to the distal end member, the stopper portion being fixed to the electrode distal end portion via the columnar portion and substantially having the shape of a solid of revolution centered on a center axis of the electrode member. The distal end member has a tapered inner surface that abuts against the stopper portion in the longitudinal axis direction when the electrode member is maximally moved forward from a distal end of the distal end member, the tapered inner surface narrowing toward the distal end. A recessed portion that constitutes a channel through which the liquid can be distributed in a state in which the tapered inner surface and the stopper portion abut against each other is formed in the stopper portion, the recessed portion being formed in a portion in a circumferential direction about the center axis. Distribution of the liquid is limited such that the liquid flows out toward a distal end side of the stopper portion only through the recessed portion as the entire circumference of the stopper portion except for the recessed portion abuts against the tapered inner surface. The electrode distal end portion has a small-diameter portion in at least part in a circumferential direction, the small-diameter portion being recessed in a radial direction of the electrode distal end portion. The channel constituted by the recessed portion and the small-diameter portion are located at the same position in the circumferential direction, and the small-diameter portion is located in front of the liquid flowing out from the recessed portion in the longitudinal axis direction so that the liquid is released in a straight line in the forward direction through the small-diameter portion even when the electrode member is rotated about the center axis.

DESCRIPTION OF EMBODIMENTS

A high-frequency treatment tool 1 according to an embodiment of the present invention will now be described with reference to the drawings.

Figure 1:
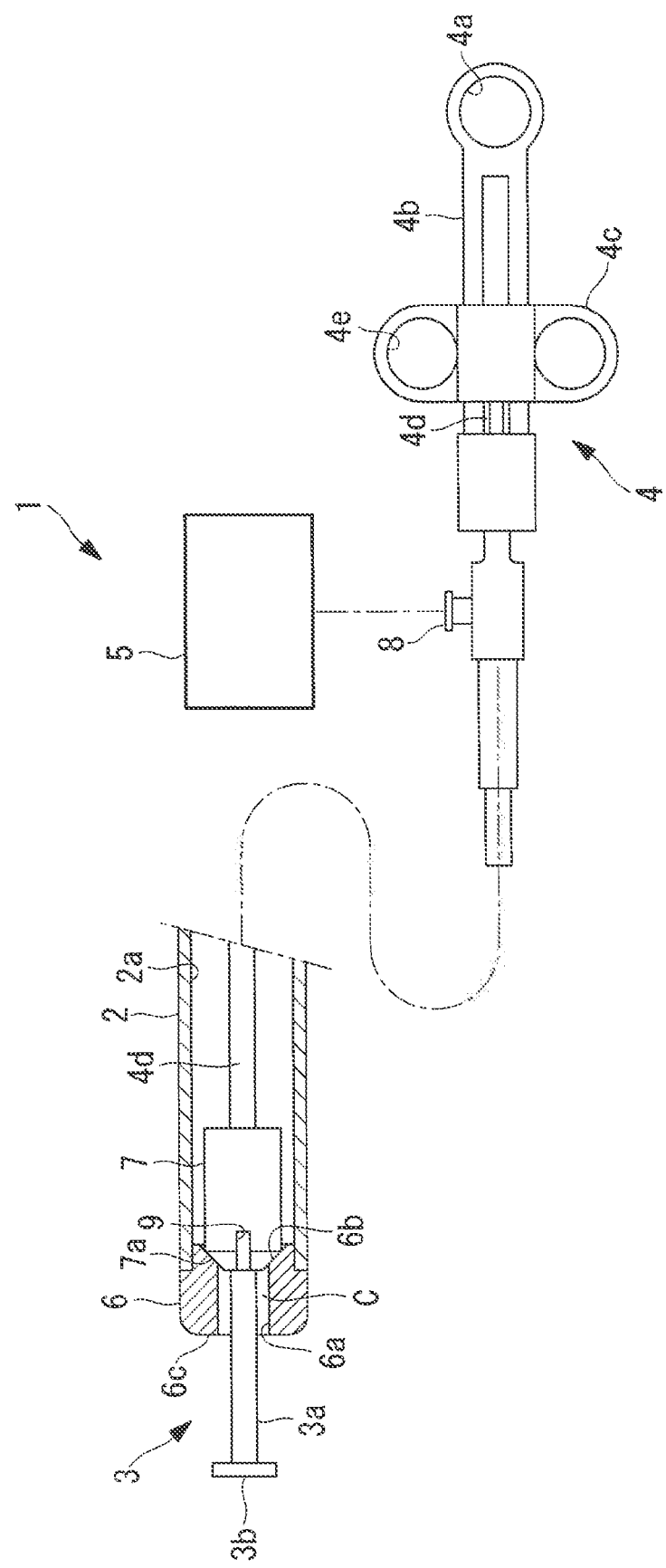
FIG. 1 is an enlarged overview diagram of a distal end portion of a high-frequency treatment tool according to an embodiment of the present invention, in which some portion is omitted from the drawing.

The high-frequency treatment tool 1 according to this embodiment is, for example, a treatment tool whose distal end is guided into the body through a channel provided in an insertion unit of an endoscope. As illustrated in FIG. 1, the high-frequency treatment tool 1 is equipped with a flexible sheath 2 formed to have an elongated cylindrical shape that is insertable into a channel; an advancable and retractable electrode member 3 at a distal end of the sheath 2; an operation unit 4 at a proximal end of the sheath 2, the operation unit being configured to push and pull the electrode member 3; and a liquid feeding unit 5 that causes a liquid to be released from the distal end of the sheath 2 via an inner cavity (channel) 2a of the sheath 2.

Figure 2:
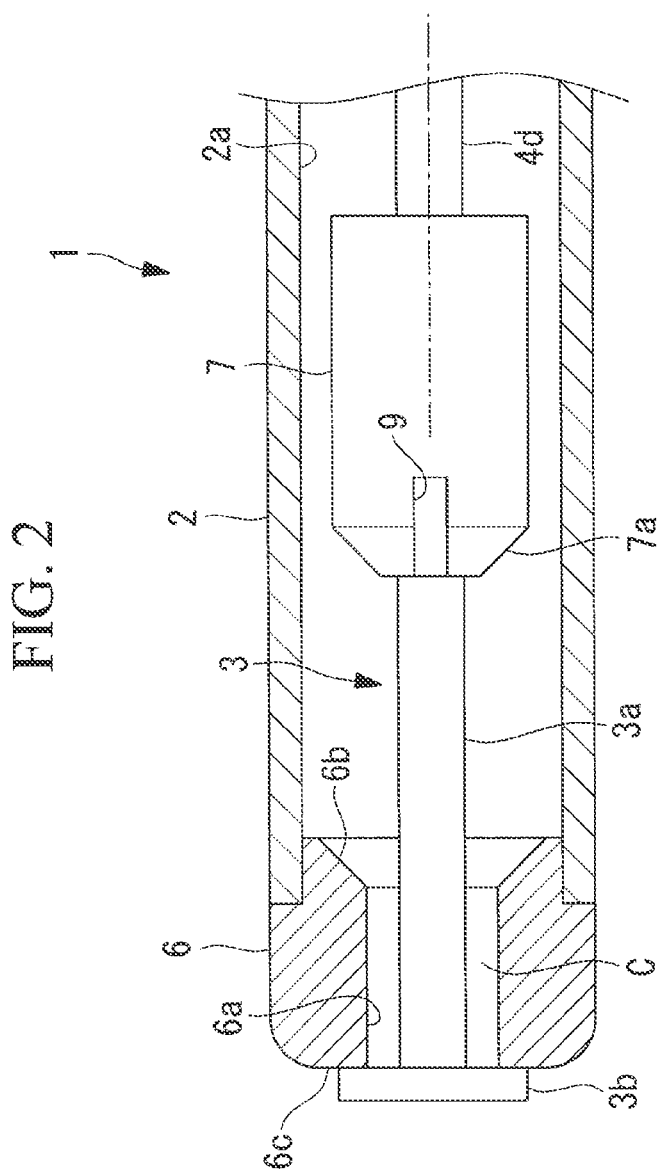
FIG. 2 is an enlarged longitudinal sectional view of the distal end portion in a state in which an electrode member of the high-frequency treatment tool is maximally retracted.

A plug-shaped distal end member 6 is fixed to the distal end of the sheath 2 so as to close the inner cavity 2a. As illustrated in FIG. 2, the distal end member 6 has a through hole 6a penetrating in the longitudinal axis direction. The through hole 6a allows the electrode member 3 to pass therethrough and move therein. The through hole 6a has a circular cross section, and a tapered inner surface 6b having the shape of an inner surface of a circular cone that narrows toward the distal end is provided on the proximal end of the through hole 6a. The sheath 2 and the distal end member 6 are composed of an electrically insulating material.

The electrode member 3 is composed of a conductive material. The electrode member 3 includes a columnar portion 3a that has a diameter sufficiently smaller than that of the through hole 6a and has a circular cross section; a triangular flat plate-shaped electrode distal end portion 3b that is provided at the distal end of the columnar portion 3a and radially extends in a radially outward direction; and a stopper portion 7 that is provided at the proximal end of the columnar portion 3a and has a columnar shape having a cross-sectional shape larger in diameter than the columnar portion 3a and being concentric with the columnar portion 3a. The stopper portion 7 has a tapered surface 7a at the distal end, the tapered surface 7a having a shape complementary to the tapered inner surface 6b.

Figure 3:
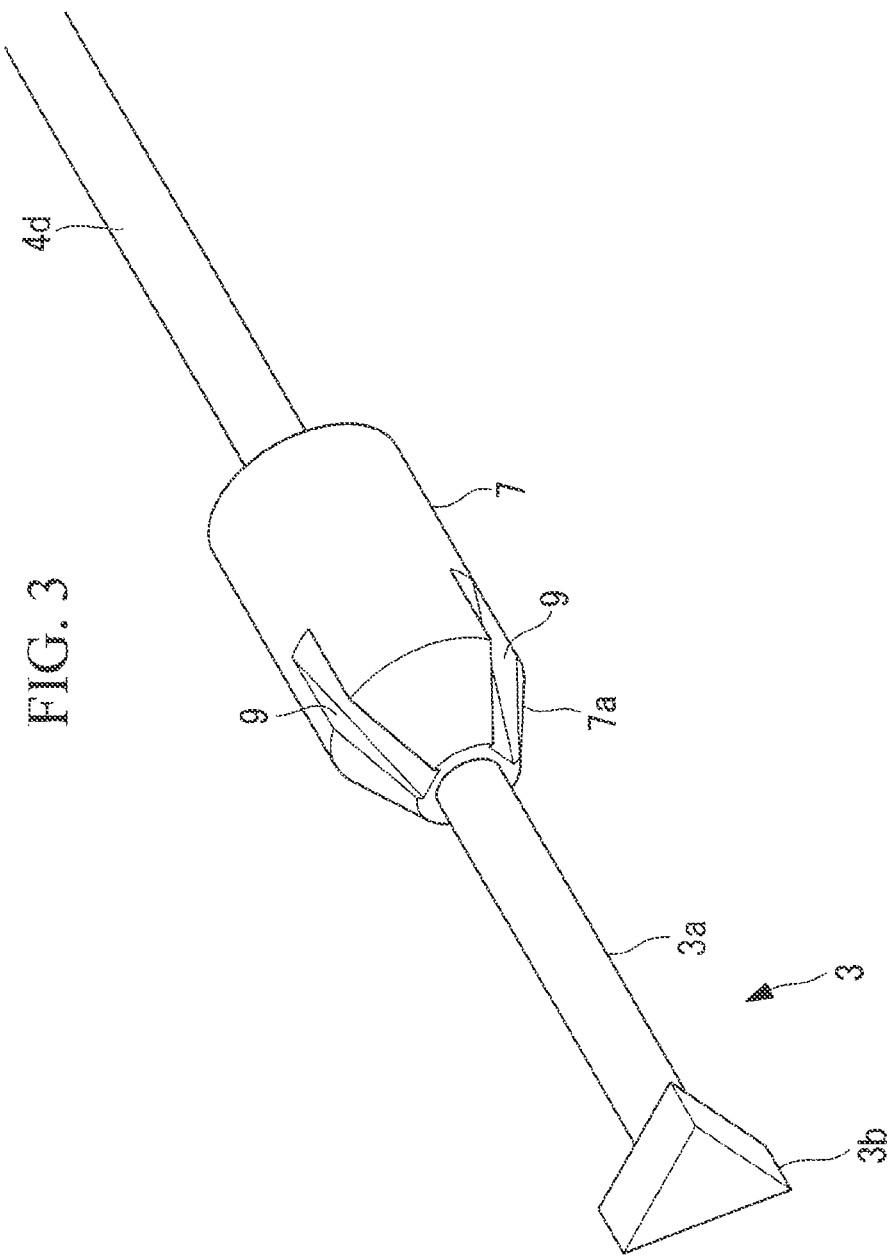
FIG. 3 is a perspective view of the electrode member of the high-frequency treatment tool illustrated in FIG. 1.

Groove-shaped recessed portions 9 that are recessed in the radially inward direction and extend in the longitudinal axis direction are respectively provided in the tapered surface 7a at three positions spaced from one another in the circumferential direction. As illustrated in FIG. 3, the recessed portions 9 lie at positions that respectively correspond to the centers of the sides of the triangular electrode distal end portion 3b in the circumferential direction.

Figure 4:
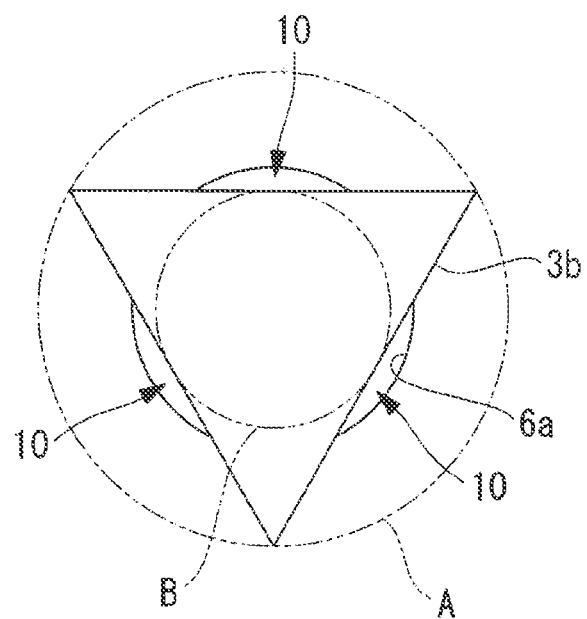
FIG. 4 is a front view illustrating the relationship between the electrode distal end portion of the high-frequency treatment tool and the through hole in the supporting member.

As illustrated in FIG. 4, the electrode distal end portion 3b has such a shape that the circumscribed circle A is larger than the through hole 6a, and the inscribed circle B is smaller than the through hole 6a. Preferably, the circumscribed circle A has a diameter of 1.2 and the through hole 6a has a diameter of 0.8. In this manner, when the electrode member 3 is maximally moved toward the proximal end with respect to the distal end member 6, most of the electrode member 3 becomes housed inside the sheath 2, and the rear surface of the electrode distal end portion 3b abuts a distal end surface 6c of the distal end member 6 so that further retraction is restricted. Here, as illustrated in FIG. 4, the circular through hole 6a is prevented from becoming fully closed by the electrode distal end portion 3b, and protrudes in the radially outward direction from the electrode distal end portion 3b so as to partially open so as to form an opening 10.

As illustrated in FIG. 1, when the electrode distal end portion 3b is maximally moved toward the distal end with respect to the distal end member 6, the electrode member 3 protrudes forward from the distal end surface 6c of the distal end member 6, and the tapered surface 7a of the stopper portion 7 abuts the tapered inner surface 6b of the distal end member 6 so that further advancement is restricted. Here, the tapered surface 7a having a shape complementary to the tapered inner surface 6b makes close contact with the tapered inner surface 6b by surface contact, so that the electrode member 3 is firmly supported by the distal end member 6. In addition, when the tapered surface 7a concentric with the columnar portion 3a of the electrode member 3 is brought into close contact with the tapered inner surface 6b connected to the through hole 6a, the center axis of the electrode member 3 becomes coincident with that of the through hole 6a (in other words, centering is achieved).

The operation unit 4 includes a handle 4b that has a finger hole 4a and is installed at the proximal end of the sheath 2; a movable unit 4c that can move relative to the handle 4b in the longitudinal axis direction of the sheath 2; and a wire 4d that is disposed in the inner cavity 2a of the sheath 2 and is composed of a conductive material that connects the movable unit 4c and the electrode member 3 to each other. In the drawing, reference numeral 4e denotes a finger hole formed in the movable unit 4c.

When the movable unit 4c is moved toward the distal end of the sheath 2 with respect to the handle 4b, a pressing force is transmitted to the electrode member 3 via the wire 4d, and the electrode member 3 advances with respect to the distal end member 6. When the movable unit 4c is moved toward the proximal end of the sheath 2 with respect to the handle 4b, a pressing force is transmitted to the electrode member 3 via the wire 4d, and the electrode member 3 is retracted to be withdrawn into the through hole 6a of the distal end member 6 of the electrode member 3.

A power supply (not illustrated in the drawing) is connected to the proximal end of the wire 4d so that high-frequency current can be supplied to the electrode member 3 via the wire 4d.

The handle 4b has a connecting port 8 in communication with the inner cavity 2a of the sheath 2.

The liquid feeding unit 5 is a syringe, a pump, or the like, connected to the connecting port 8, and is configured to feed a liquid, such as saline, into the inner cavity 2a of the sheath 2 by activation of the liquid feeding unit 5.

The effects of the high-frequency treatment tool 1 of this embodiment configured as described above will now be described.

Endoscopic submucosal dissection is performed by using the high-frequency treatment tool 1 of this embodiment as follows. The operation unit 4 is operated so that, as illustrated in FIG. 4, the sheath 2 is guided into the body from the distal end of the sheath 2 through a channel in the insertion unit of an endoscope while the electrode member 3 is being maximally retracted, and then the distal end of the sheath 2 is allowed to protrude from the distal end of the insertion unit of the endoscope.

As a result, the distal end portion of the sheath 2 enters the view of the endoscope, and the operator performs treatment by checking the image on a monitor screen acquired by the endoscope. When the electrode member 3 is maximally retracted, only the electrode distal end portion 3b of the electrode member 3 is exposed at the distal end surface 6c of the distal end member 6. Thus, even when high-frequency current is applied to the electrode member 3 under this condition, tissues are prevented from becoming deeply incised, and what is known as marking, i.e., cauterizing only the tissue surfaces, can be performed.

In other words, the operator presses the distal end surface 6c of the distal end member 6 against portions that surround what appears to be a lesion to be excised in an endoscopic image displayed on a monitor screen, and electrifies the electrode member 3 so as to form a mark that surrounds the lesion to be excised and that serves as a guide for the subsequent treatment.

Subsequently, the operation unit 4 is operated so that, as illustrated in FIG. 3, the electrode member 3 is allowed to protrude from the distal end surface 6c of the distal end member 6, and high-frequency current is applied to incise the tissue and insert the distal end member 6 to a portion near the submucosal layer under the lesion. Next, the operation unit 4 is operated so as to create a state in which the electrode member 3 is maximally retracted, and the liquid feeding unit 5 is activated so as to release a liquid, such as saline, from the opening 10 in the distal end surface 6c. As a result, the liquid is locally injected to the submucosal layer, and the lesion becomes afloat.

Under this condition, the sheath 2 is withdrawn from the submucosal layer, the operation unit 4 is again operated so that the electrode member 3 is made to protrude, and then the tissue around the lesion is incised by using, as a guide, the mark formed by the marking.

In the event of bleeding during incising, the liquid feeding unit 5 is activated so that a liquid, such as saline, is released from the opening 10 in the distal end surface 6c of the distal end member 6 so as perform washing.

In such a case, the electrode member 3 is maximally advanced with respect to the sheath 2, and the electrode distal end portion 3b is made to protrude from the distal end surface 6c of the distal end member 6. As a result, the tapered surface 7a of the stopper portion 7 makes close contact with the tapered inner surface 6b of the distal end member 6, and the electrode member 3 becomes fixed while being centered with respect to the through hole 6a. Even in a state in which the tapered surface 7a and the tapered inner surface 6b are brought into close contact with each other, the respective spaces in front of and behind the stopper portion 7 remain in communication with each other due to the recessed portions 9 formed in the tapered surface 7a.

Under this condition, when the liquid feeding unit 5 is activated, the liquid sent through the inner cavity 2a of the sheath 2 passes through gaps C formed by the recessed portions 9 and between the tapered surface 7a and the tapered inner surface 6b, then passes through a cylindrical gap C between the columnar portion 3a and the through hole 6a, and is released to the anterior of the distal end member 6.

The flow of the fluid flowing in the gap C between the columnar portion 3a and the through hole 6a generates the force that causes the columnar portion 3a to vibrate. However, since the tapered surface 7a is in close contact with the tapered inner surface 6b and thus the electrode member 3 is firmly supported by the distal end member 6, vibration of the columnar portion 3a is suppressed, and the fluid can be stably released to the anterior of the distal end member 6.

In other words, even when the inner diameter of the through hole 6a is sufficiently large relative to the outer diameter of the columnar portion 3a, the columnar portion 3a is supported as a result of the close contact between the tapered surface 7a and the tapered inner surface 6b to prevent vibration of the columnar portion 3a. Thus, there is an advantage in that it becomes possible to secure a sufficiently large flow area between the through hole 6a and the columnar portion 3a, and the fluid can be smoothly released at a high flow rate. Thus, blood can be more assuredly and rapidly washed away.

Furthermore, since there is no need to support the columnar portion 3a by the through hole 6a to prevent vibration in the radial direction, there is an advantage in that the through hole 6a itself can be formed to have a simple circular cross section with an inner diameter sufficiently larger than the outer diameter of the columnar portion 3a, which makes the production thereof easier.

During incising of the tissue surrounding the lesion, the liquid locally injected to the submucosal layer may become absorbed by other regions, and the lesion may start to sink down. In that case, the distal end member 6 is again pressed against the submucosal layer to locally inject the liquid. In this case also, since the liquid is released while having the electrode member 3 maximally retracted, the electrode member 3 does not penetrate the tissue beyond what is necessary.

In this case also, according to the high-frequency treatment tool 1 of this embodiment, when the electrode member 3 is maximally retracted so that the electrode distal end portion 3b abuts the distal end surface 6c of the distal end member 6, the large through hole 6a protrudes from the electrode distal end portion 3b in the radially outward direction and remains open. Thus, the liquid can be released from this opening 10. In particular, since the recessed portions 9 formed in the tapered surface 7a and portions of the electrode distal end portion 3b that have small protruding amounts in the radial direction (small-diameter portions) have matching phases, the fluid that flowed through the recessed portions 9 is not completely blocked by the electrode distal end portion 3b and can be smoothly released forward.

In this embodiment, the electrode distal end portion 3b has a triangular flat plate shape. However, the shape is not limited to this, and any electrode distal end portion 3b that has radially protruding portions and radially recessed portions alternately arranged in the circumferential direction, such as a polygonal shape having four or more sizes, a star shape, or an elliptical shape, may be employed. Any shape may be employed as long as the circumscribed circle A of these shapes is larger than the through hole 6a and the inscribed circle B is smaller than the through hole 6a. In such cases, it is preferable to form groove-shaped recessed portions 9 at positions that correspond to the radially recessed portions (small-diameter portions).

Figure 5:
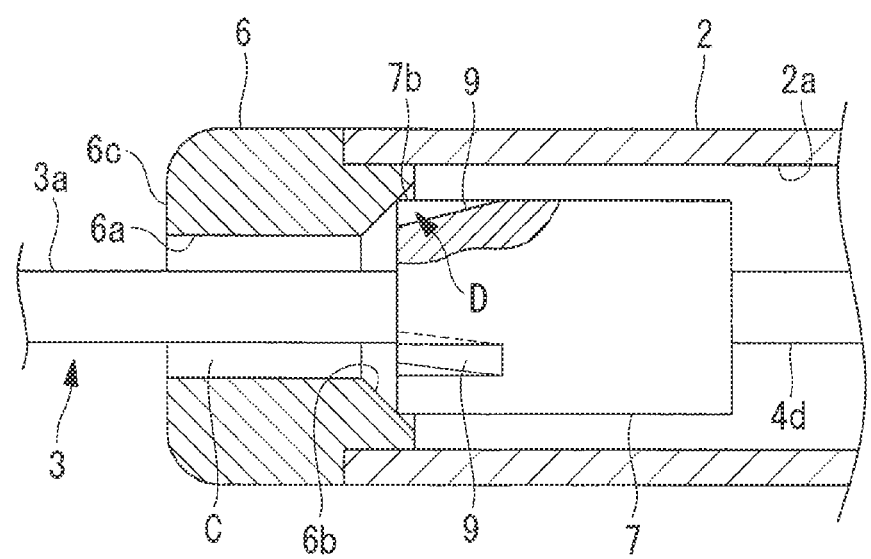
FIG. 5 is a longitudinal sectional view of a part of the distal end portion according to a modification of the high-frequency treatment tool illustrated in FIG. 1.
Figure 6:
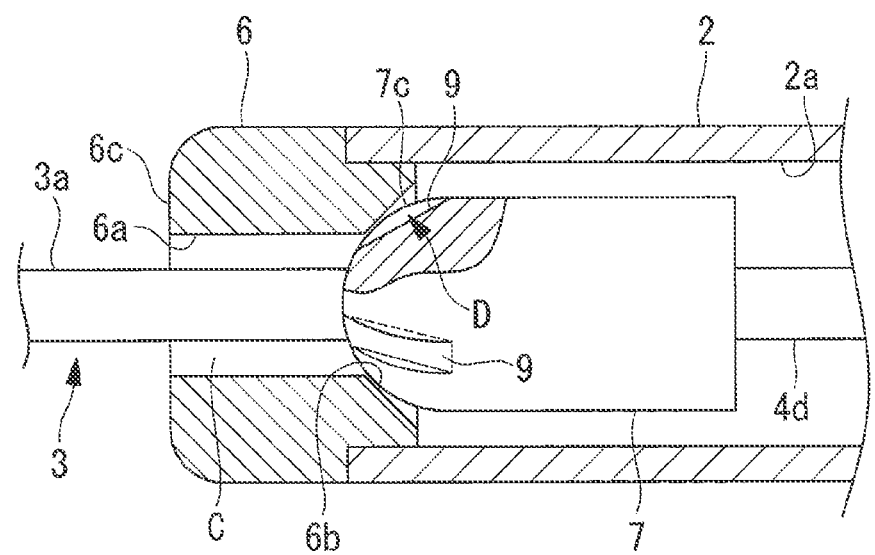
FIG. 6 is a longitudinal sectional view of a part of the distal end portion according to another modification of the high-frequency treatment tool illustrated in FIG. 1.

In this embodiment, the stopper portion 7 that has the tapered surface 7a that surface-contacts the tapered inner surface 6b is described as an example; alternatively, as illustrated in FIGS. 5 and 6, a stopper portion that has the shape of a solid of revolution, such as a columnar edge 7b or a spherical surface 7c, and makes linear contact with the tapered inner surface 6b in an annular manner may be employed instead of the tapered surface 7a.

Figure 7:
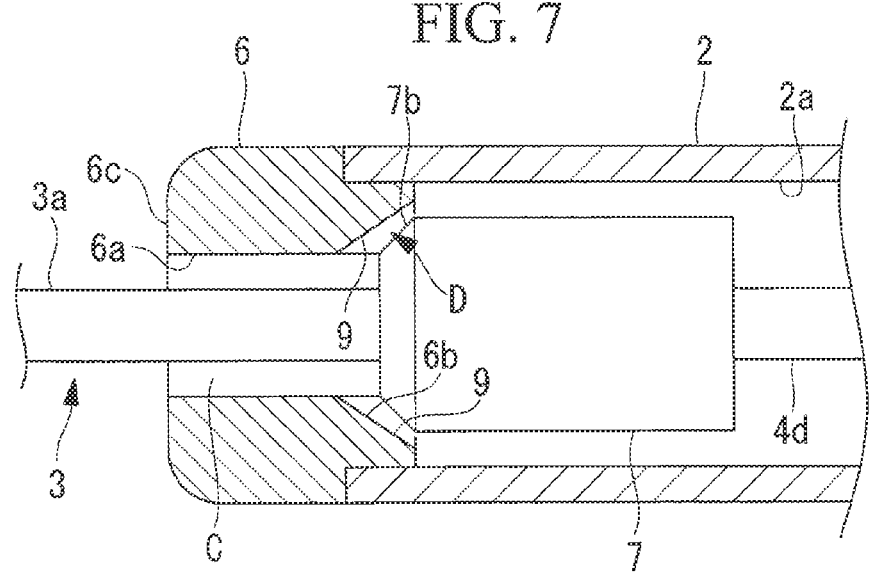
FIG. 7 is a longitudinal sectional view of a part of the distal end portion according to another modification of the high-frequency treatment tool illustrated in FIG. 1.

Moreover, although the groove-shaped recessed portions 9 that enable distribution of a fluid between the tapered inner surface 6b and the tapered surface 7a in close contact with each other are formed in the tapered surface 7a, the recessed portions 9 may be formed in the tapered inner surface 6b, as illustrated in FIG. 7, instead.

Figure 8:
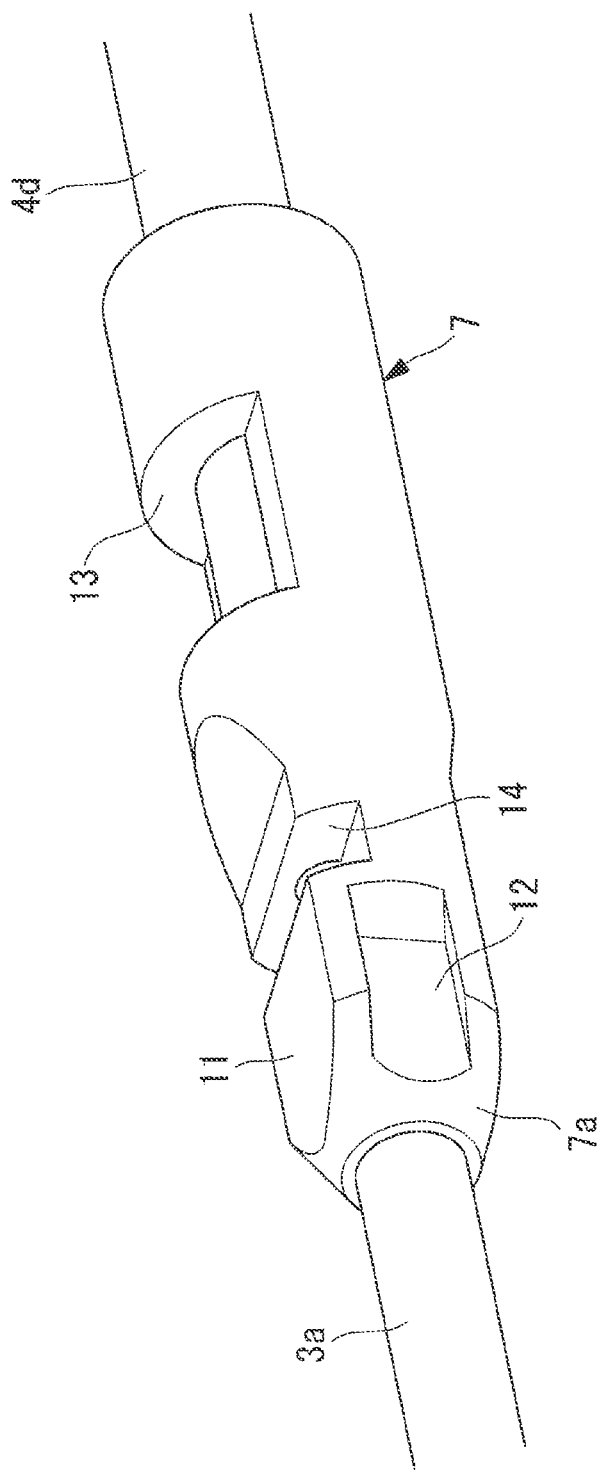
FIG. 8 is a perspective view of the stopper portion according to another modification of the high-frequency treatment tool illustrated in FIG. 1.
Figure 9:
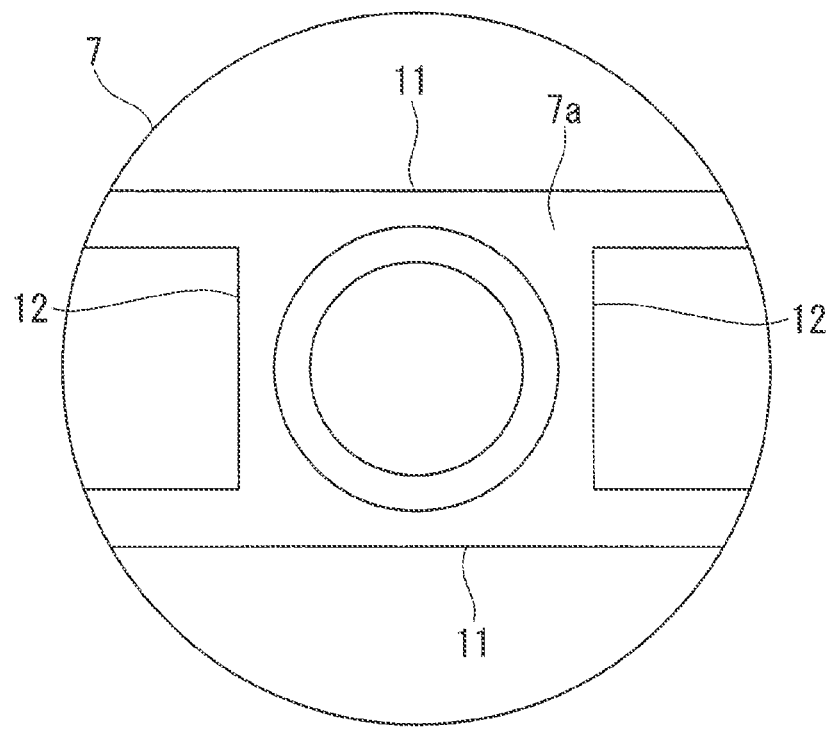
FIG. 9 is a cross-sectional view of the distal end portion of the stopper portion illustrated in FIG. 8.

In this embodiment, the recessed portions 9 of the stopper portion 7 have a groove shape, but this is not limiting. As illustrated in FIGS. 8 and 9, a D cut portion 11 that extends along the longitudinal axis direction of the sheath 2 and grooves 12 that flank the D cut portion 11 about the longitudinal axis of the sheath 2 and are equally spaced from each other may be employed instead of the recessed portions 9. Reference numeral 13 denotes a hole formed to enable brazing the wire 4d to the stopper portion 7, and reference numeral 14 denotes a hole formed to enable brazing the columnar portion 3a to the stopper portion 7.

Figure 10:
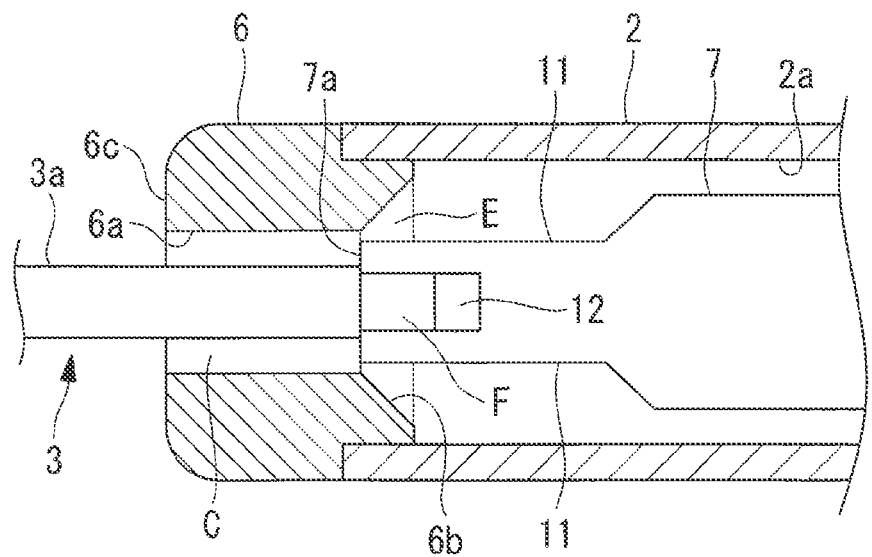
FIG. 10 is a longitudinal sectional view of a part of the distal end portion of the high-frequency treatment tool illustrated in FIG. 8.

In this case, as illustrated in FIG. 10, a gap E is formed between the tapered surface 7a and the tapered inner surface 6a by the D cut portion 11, and a gap F is formed between the tapered surface 7a and the tapered inner surface 6a by the grooves 12. In this manner, the gap E formed by the D cut portion 11 wider than the grooves 12 allows a higher flow rate per unit time than the gap F formed by the groove 12. Thus, the total flow rate per unit time can be increased by using the entire circumference of the stopper portion 7.

As a result, the above-described embodiment leads to the following aspect.

An aspect of the present invention provides a high-frequency treatment tool that includes an elongated cylindrical sheath to be inserted into a body; a straight bar-shaped electrode member to which high-frequency current is to be supplied, the electrode member being disposed so as to be advancable and retractable in the sheath in a longitudinal axis direction; a distal end member that is disposed at a distal end side of the sheath and that has a through hole through which the electrode member is passed; and a liquid feeding unit that is connected to a proximal end of the sheath that is configured to release a liquid forward in the longitudinal axis direction of the sheath through a channel formed in the sheath and a gap between the electrode member and the through hole in communication with the channel. The electrode member includes a bar-shaped columnar portion; an electrode distal end portion being provided at a distal end of the columnar portion and radially extending in a radially outward direction; and a stopper portion disposed at a proximal end side of the columnar portion with respect to the distal end member, the stopper portion being fixed to the electrode distal end portion via the columnar portion and substantially having the shape of a solid of revolution centered on a center axis of the electrode member. The distal end member has a tapered inner surface that abuts against the stopper portion in the longitudinal axis direction when the electrode member is maximally moved forward from a distal end of the distal end member, the tapered inner surface narrowing toward the distal end. A recessed portion that constitutes a channel through which the liquid can be distributed in a state in which the tapered inner surface and the stopper portion abut against each other is formed in the stopper portion, the recessed portion being formed in a portion in a circumferential direction about the center axis. Distribution of the liquid is limited such that the liquid flows out toward a distal end side of the stopper portion only through the recessed portion as the entire circumference of the stopper portion except for the recessed portion abuts against the tapered inner surface. The electrode distal end portion has a small-diameter portion in at least part in a circumferential direction, the small-diameter portion being recessed in a radial direction of the electrode distal end portion. The channel constituted by the recessed portion and the small-diameter portion are located at the same position in the circumferential direction, and the small-diameter portion is located in front of the liquid flowing out from the recessed portion in the longitudinal axis direction so that the liquid is released in a straight line in the forward direction through the small-diameter portion even when the electrode member is rotated about the center axis.

Treatment, such as incision of body tissue, is performed by increasing the protruding amount of the electrode distal end portion by advancing the electrode member with respect to the sheath and then supplying high-frequency current to the electrode member. In performing incision or detachment of tissue, the radially extending electrode distal end portion is hooked to the surrounding tissue so that the treatment can be performed stably without slipping.

Under this condition, when the electrode member is advanced, the stopper portion disposed on the proximal end of the electrode member abuts the tapered inner surface of the distal end member disposed at the distal end of the sheath and allowing the electrode to pass through the through hole, and thus further advancement is restricted. Since the stopper portion is formed to substantially have the shape of a solid of revolution, when the stopper portion abuts the tapered inner surface, portions of the stopper portion at positions surrounding the electrode member abut against the tapered inner surface simultaneously so that the electrode member can remain centered with respect to the through hole.

During the course of this, the recessed portion formed in the tapered inner surface or the stopper portion forms a channel between the tapered inner surface and the stopper portion abutting against each other. When bleeding occurs in the site being treated, the liquid feeding unit is activated so that a liquid is released forward in the longitudinal axis direction of the sheath through the channel formed in the sheath and a gap between the electrode member and the through hole in the distal end member at the distal end of the sheath, and, as a result, the liquid can be released near the bleeding site so as to perform washing.

Moreover, the channel, which is formed by the recessed portion when the stopper portion and the tapered inner surface abut against each other, and the small-diameter portion of the electrode distal end portion are always maintained to be in phase with each other. Even when the electrode distal end portion is rotated about the longitudinal axis with respect to the through hole, the liquid released from the channel can always be released in a straight line in the forward direction through the small-diameter portion of the electrode distal end portion.

In this case also, the electrode member is firmly supported since the tapered inner surface and the stopper portion abut against each other at positions that surround the electrode member; thus, even when a liquid flows in the gap between the electrode member and the through hole, the electrode distal end portion is held so as not to vibrate.

In other words, according to this aspect, the electrode member is not supported by the through hole; alternatively, the tapered inner surface disposed in the distal end member and the stopper portion disposed in the electrode member contact each other so as to enable centering and firm support. Thus, a sufficiently large gap can be secured between the through hole and the electrode member. As a result, the liquid released forward via the gap can be released without being obstructed by the electrode distal end portion and without vibration of the electrode member.

In the aspect described above, the stopper portion may have a tapered surface that is brought into surface-contact with the tapered inner surface.

In this manner, due to the surface contact between the stopper portion and the tapered inner surface, the electrode member centered in the through hole can be more firmly supported by the distal end portion.

In the aspect described above, a distal end opening of the through hole may have a circular projection shape in the longitudinal axis direction, and a projection shape of the electrode distal end portion in the longitudinal axis direction may have a non-circular shape constituted by a circumscribed circle larger than a bore of the distal end opening and an inscribed circle smaller than the bore.

In this manner, when the electrode member is maximally retracted with respect to the sheath, a portion of the non-circular electrode distal end portion protruding in the radial direction abuts against the distal end surface of the distal end member with respect to the distal end opening of the circular through hole, and further retraction is restricted. In addition, the distal end opening of the circular through hole has portions protruding in the radial direction from the non-circular electrode distal end portion, and through these portions, the liquid released from the distal end opening is released in a straight line in the forward direction without being completely blocked by the electrode distal end portion.

In the aspect described above, the recessed portion may be formed in the stopper portion.

In this manner, the channel, which is formed by the recessed portion when the stopper portion and the tapered inner surface abut against each other, and the electrode distal end portion are always maintained in phase with each other. Even when the electrode distal end portion is rotated about the longitudinal axis with respect to the through hole, changes in the channel caused by the electrode distal end portion are prevented.

In the aspect described above, the small-diameter portion may include a plurality of small-diameter portions equally spaced from one another in a circumferential direction, and the recessed portions may be disposed at positions that correspond to the small-diameter portions.

In this manner, the flow of the liquid released in a straight line toward the anterior of the electrode distal end portion through the recessed portions and the small-diameter portions can be prevented from becoming uneven in the circumferential direction of the electrode distal end portion and can be released forward in a more straight manner.

In the aspect described above, the distal end member may be an electrically insulating member protruding from a distal end of the sheath.

In the aspect described above, the recessed portion has the shape of a groove that extends in the longitudinal axis direction.

The advantageous effects of the present invention are that smooth liquid feeding and stable electrode support can both be achieved, and production is facilitated.

REFERENCE SIGNS LIST 1 high-frequency treatment tool
2 sheath
2a inner cavity (channel)
3 electrode member
3b electrode distal end portion
5 liquid feeding unit
6 distal end member
6a through hole
6b tapered inner surface
7 stopper portion
7a tapered surface
9 recessed portion
C gap

The invention claimed is:

1. A high-frequency treatment tool comprising:
an elongated cylindrical sheath configured to be inserted into a body;
a straight bar-shaped electrode member to which high-frequency current is supplied, the electrode member being disposed so as to be advancable and retractable in the sheath in a longitudinal axis direction;
a distal end member disposed at a distal end of the sheath, the distal end member having a through hole through which the electrode member is passed; and
an inlet disposed on a proximal end side of the sheath, the inlet being in fluid communication with a channel formed in the sheath such that a liquid flowing into the inlet flows into the channel and through a gap formed between the electrode member and the through hole in fluid communication with the channel,
wherein the electrode member includes:
a bar-shaped columnar portion;
an electrode distal end portion provided at a distal end of the columnar portion, the electrode distal end portion extending outward in a radial direction; and
a stopper disposed at a proximal end side of the columnar portion with respect to the distal end member, the stopper being fixed to the electrode distal end portion via the columnar portion and substantially having the shape of a solid of revolution centered on a center axis of the electrode member,
wherein the distal end member comprises:
a tapered inner surface having a distal portion narrower in the radial direction than a proximal portion, the tapered inner surface being configured to abut against the stopper in the longitudinal axis direction in an abutment state in which the electrode member is maximally moved forward from a distal end of the distal end member;
a recess configured to form a channel in the stopper through which the liquid can be distributed in the abutment state, the recess being formed in a portion in a circumferential direction about the center axis, in the abutment state, an entire circumference of the stopper except for the recess abuts against the tapered inner surface such that flow of the liquid flows out from a distal end side of the stopper only through the recess,
a small-diameter portion formed in at least part of the electrode distal end portion in a circumferential direction, the small-diameter portion being recessed inwardly in the radial direction of the electrode distal end portion, the small diameter portion being positioned distally of the liquid flowing out from the recessed portion in the longitudinal axis direction, and
wherein the small diameter portion and the recess are aligned in the circumferential direction such that even when the electrode member is rotated about the center axis, the liquid flows in a straight line in the distal direction from the recess and through the small-diameter portion.

2. The high-frequency treatment tool according to claim 1, wherein the stopper has a tapered surface that is brought into surface-contact with the tapered inner surface.

3. The high-frequency treatment tool according to claim 1, wherein a distal end opening of the through hole has a circular projection shape in the longitudinal axis direction, and a projection shape of the electrode distal end portion in the longitudinal axis direction has a non-circular shape formed by a circumscribed circle larger than a bore of the distal end opening and an inscribed circle smaller than the bore.

4. The high-frequency treatment tool according to claim 1, wherein the small-diameter portion comprises a plurality of small-diameter portions equally spaced from one another in the circumferential direction, and
the recess comprises a plurality of recesses disposed at positions that correspond to the small-diameter portions.

5. The high-frequency treatment tool according to claim 1, wherein the distal end member is an electrically insulating member protruding from a distal end of the sheath.

6. The high-frequency treatment tool according to claim 1, wherein the recess has the shape of a groove that extends in the longitudinal axis direction.

7. The high-frequency treatment tool according to claim 1, wherein the distal end member is configured to be abutted by a proximal surface of the electrode distal end portion so as to restrict retraction of the electrode distal end portion.

8. The high-frequency treatment tool according to claim 1, wherein the through hole is configured to protrude outwardly in the radial direction from the electrode distal end portion so as to form a partial opening.

9. The high-frequency treatment tool according to claim 1, wherein in the abutment state, the tapered inner surface is configured to align the center axis of the electrode member with a center axis of the through hole.

* * * * *